United States Patent
Ono

(10) Patent No.: US 10,113,155 B2
(45) Date of Patent: Oct. 30, 2018

(54) STEVIOL GLYCOSYLTRANSFERASE AND GENE ENCODING SAME

(71) Applicant: SUNTORY HOLDINGS LIMITED, Osaka (JP)

(72) Inventor: Eiichiro Ono, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 796 days.

(21) Appl. No.: 14/402,165

(22) PCT Filed: May 29, 2013

(86) PCT No.: PCT/JP2013/065518
§ 371 (c)(1),
(2) Date: Nov. 19, 2014

(87) PCT Pub. No.: WO2013/180306
PCT Pub. Date: Dec. 5, 2013

(65) Prior Publication Data
US 2015/0218533 A1    Aug. 6, 2015

(30) Foreign Application Priority Data
May 30, 2012    (JP) ................. 2012-123349

(51) Int. Cl.
| C12N 9/10 | (2006.01) |
| C07K 14/415 | (2006.01) |
| C12P 19/44 | (2006.01) |
| C12N 15/82 | (2006.01) |
| C12P 19/56 | (2006.01) |
| C12P 15/00 | (2006.01) |

(52) U.S. Cl.
CPC ....... *C12N 9/1051* (2013.01); *C12N 15/8245* (2013.01); *C12P 15/00* (2013.01); *C12P 19/56* (2013.01); *C12Y 204/01* (2013.01)

(58) Field of Classification Search
CPC .. C12N 9/1051; C12N 9/1048; C12Y 204/01; A23V 2250/258; A23V 2250/262
See application file for complete search history.

(56) References Cited

U.S. PATENT DOCUMENTS

| 4,219,571 A | 8/1980 | Miyake |
| 4,590,160 A | 5/1986 | Nishihashi et al. |
| 4,892,938 A * | 1/1990 | Giovanetto ............ A61K 36/28 536/127 |
| 6,982,077 B2 * | 1/2006 | Hammer ................. A61K 8/26 424/401 |
| 9,115,166 B2 | 8/2015 | Prakash et al. |
| 9,243,273 B2 | 1/2016 | Markosyan et al. |
| 9,562,251 B2 | 2/2017 | Kishore et al. |
| 2008/0064063 A1 | 3/2008 | Brandle et al. |
| 2008/0148432 A1 | 6/2008 | Abad |
| 2010/0316782 A1 | 12/2010 | Shi et al. |
| 2011/0189717 A1 | 8/2011 | Ajikumar et al. |
| 2012/0107893 A1 | 5/2012 | Ajikumar et al. |
| 2012/0164678 A1 | 6/2012 | Stephanopoulos et al. |
| 2014/0017378 A1 | 1/2014 | Purkayastha et al. |
| 2014/0030381 A1 | 1/2014 | Markysyan |
| 2014/0357588 A1 | 12/2014 | Markosyan et al. |
| 2016/0186225 A1 | 6/2016 | Mikkelsen et al. |

FOREIGN PATENT DOCUMENTS

| EP | 1 897 951 | 12/2010 |
| JP | 54-030199 | 3/1979 |
| JP | 62-155096 A | 7/1987 |
| JP | 5-255372 | 10/1993 |
| JP | 2011-512801 A | 4/2011 |
| WO | 2008/034648 | 3/2008 |
| WO | 2012/075030 | 6/2012 |
| WO | 2013/176738 | 11/2013 |

OTHER PUBLICATIONS

Richman, Alex, et al. "Functional genomics uncovers three glucosyltransferases involved in the synthesis of the major sweet glucosides of Stevia rebaudiana." The Plant Journal 41.1 (2005): 56-67.*
Noguchi, Akio, et al. "Local differentiation of sugar donor specificity of flavonoid glycosyltransferase in Lamiales." The Plant Cell 21.5 (2009): 1556-1572.*
Kinghorn, A. Douglas, ed. Stevia: the genus Stevia. CRC Press, 2003 (Year: 2003).*
Richman, Alex, et al. "Functional genomics uncovers three glucosyltransferases involved in the synthesis of the major sweet glucosides of Stevia rebaudiana." The Plant Journal41.1 (2005): 56-67. (Year: 2005).*
Shibata et al., "Steviol and steviol-glycoside: glycosyltransferase activities in *Stevia rebaudiana* Betoni—purification and partial characterization", *Arch. Biochem. Biophys.*, vol. 321, No. 2, pp. 390-396 (1995).
Brandle et al., "Steviol glycoside biosynthesis", *Phytochemistry*, vol. 68, No. 14, pp. 1855-1863 (2007).
Richman et al., "Functional genomics uncovers three glucosyltransferases involved in the synthesis of the major sweet glucosides of Stevia rebaudiana ", *Plant J.*, vol. 41, No. 1 , 2005, pp. 56-67 (2005).
Kasai et al., "Stevia-ha no Kanmi Diterpene Haitotai-Rebaudioside-A, -D, -E Oyobi Kanren Haitotai no Gosei Narabini Kanmi to Kagaku Kozo tono Sokan-", *Journal of the Chemical Society of Japan*, No. 5, pp. 726-735 (1981), including English language Abstract.
Mizutani et al., "Diversification of P450 genes during land plant evolution ", *Annu. Rev. Plant Biol.*, vol. 61, pp. 291-315 (2010).

(Continued)

*Primary Examiner* — Lee A Visone
*Assistant Examiner* — Weihua Fan
(74) *Attorney, Agent, or Firm* — Greenblum & Bernstein, P.L.C.

(57) ABSTRACT

The present invention provides steviol glycosyltransferase and a method for producing a steviol glycoside using this enzyme. The present invention provides a transformant transformed with a gene for steviol glycosyltransferase and a method for preparing such a transformant.

17 Claims, 6 Drawing Sheets

Specification includes a Sequence Listing.

(56) References Cited

OTHER PUBLICATIONS

Ono et al., "Diterpene Kanmiryo Rebaudioside A no Seigosei ni Kakawaru Stevia Shinki Haitotaika Koso no Dotei", Dai 54 Kai Proceedings of the Annual Meeting of the Japanese Society of Plant Physiologists, 3aH10 (464), Mar. 14, 2013, p. 230.
U.S. Appl. No. 14/386,934 to Eiichiro Ono, filed Sep. 22, 2014.
U.S. Appl. No. 14/383,698 to Eiichiro Ono et al., filed Sep. 8, 2014.
International Search Report for PCT/JP2013/065518, dated Jul. 9, 2013.
Tanaka, "Improvement of taste of natural sweeteners", *Pure & Appl. Chem.*, vol. 69, No. 4, pp. 675-683 (1997).
Extended European Search Report issued in EP Patent Application No. 13797812.8, dated Oct. 28, 2015.
Osmani et al., "Substrate specificity of plant UDP-dependent glycosyltransferases predicted from crystal structures and homology modeling," *Phytochemistry*, vol. 70, pp. 325-347, 2009.
Orihara et al., "Biotransformation of Steviol by Cultured Cells of *Eucalyptus perriniana* and *Coffea arabica*" *Phytochemistry*, vol. 30, No. 12, pp. 3989-3992 (1991).
Humphrey et al., "Spatial organisation of four enzymes from *Stevia rebaudiana* that are involved in steviol glycoside synthesis" *Plant Mol. Biol.*, vol. 61, pp. 47-62 (2006).

* cited by examiner

Figure 1

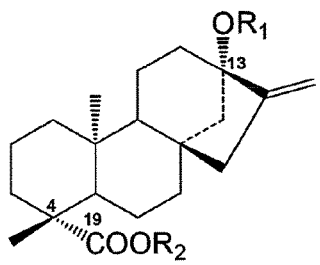

| Name | R₁ | R₂ |
|---|---|---|
| Steviol | H | H |
| Steviolmonoside | Glc | H |
| Steviolbioside | Glc-Glc(β2→1) | H |
| Dulcoside A | Glc-Rha(β2→1) | H |
| Rubusoside | Glc | Glc |
| Stevioside | Glc-Glc(β2→1) | Glc |
| Rebaudioside A | Glc-Glc(β2→1)<br>\|<br>Glc(β3→1) | Glc |
| Rebaudioside B | Glc-Glc(β2→1)<br>\|<br>Glc(β3→1) | H |
| Rebaudioside C (Dulcoside B) | Glc-Rha(β2→1)<br>\|<br>Glc(β3→1) | Glc |
| Rebaudioside D | Glc-Glc(β2→1)<br>\|<br>Glc(β3→1) | Glc-Glc(β2→1) |
| Rebaudioside E | Glc-Glc(β2→1) | Glc-Glc(β2→1) |
| Rebaudioside F | Glc-Xyl(β2→1)<br>\|<br>Glc(β3→1) | Glc |

UGT73E1HP1: UGT73E1 Homologous Protein 1

STEVIOL GLYCOSYLTRANSFERASE AND GENE ENCODING SAME

SEQUENCE LISTING

The instant application contains a Sequence Listing which has been submitted electronically in ASCII format and is hereby incorporated by reference in its entirety. Said ASCII copy, created on Mar. 10, 2015, is named P46497_SL.txt and is 12,286 bytes in size.

TECHNICAL FIELD

The present invention relates to a protein having steviol glycoside synthesis activity and a polynucleotide encoding the same, a method for producing a steviol glycoside by means of this protein, a transformant that highly expresses steviol glycosyltransferase, as well as a steviol glycoside produced by the above method and use thereof.

BACKGROUND ART

Leaves of *stevia* belonging to the family Asteraceae (*Stevia rebaudiana*) contain a secondary metabolite called steviol, a kind of diterpenoid, and steviol glycosides are used as calorie-less sweeteners in food industries because they are about 300 times sweeter than table sugar. Obesity has grown internationally as a serious social issue, and the demand for calorie-less sweeteners has been increasing day by day also in terms of health promotion and medical expense reduction. Although aspartame, an artificially synthesized amino acid derivative, and acesulfame potassium are now used as artificial sweeteners, naturally occurring calorie-less sweeteners like steviol glycosides are expected to be safer and more likely to gain public acceptance.

As a result of sugar modification, *stevia* glycoside is finally converted into a glycoside with four sugar molecules, which is called rebaudioside A (FIG. 1). Stevioside, a trisaccharide glycoside of steviol serving as a precursor of rebaudioside A, is the highest in quantity; and hence rebaudioside A and stevioside are main substances responsible for the sweetness of *stevia*. In addition to these, other glycosides which appear to be reaction intermediates and analogues with different types of sugars are known to be present.

The enzyme gene leading to biosynthesis of rebaudioside A has been isolated through expressed sequence tag (EST) analysis of *stevia* (Non-patent Documents 1 and 2, Patent Document 1). Steviol is generated when ent-kaurenoic acid, which is a precursor of the diterpenoid gibberellin serving as a plant hormone, is hydroxylated at the 13-position by the action of ent-kaurenoic acid 13-hydroxylase (EK13H), which is a cytochrome P450 enzyme (FIG. 2) (Non-patent Document 3, Patent Document 1). Steviol is first glycosylated (monoglucosylated) at the 13-position hydroxy group by the action of UGT85C2 to thereby generate steviolmonoside. Steviolmonoside is further glucosylated at the 2-position of the 13-position glucose to thereby generate a disaccharide glucoside of steviol, called steviolbioside, or is further glucosylated at the 19-position carboxyl group to thereby generate a diglucoside of steviol, called rubusoside. When the thus generated steviolbioside and rubusoside are further glucosylated, steviol glycosides including stevioside and rebaudioside A would be generated. Enzyme genes known to be involved in the generation of steviol glucosides are UGT74G1 and UGT76G1.

UGT74G1 is known to catalyze glucosylation at the 19-position of steviolmonoside (Non-patent Document 1). UGT74G1 also causes glucosylation of steviolbioside to thereby generate stevioside, a triglucoside of steviol. This stevioside is the highest in content in *stevia* leaves and is known to be about 250 to 300 times sweeter that table sugar. This stevioside is further glucosylated by the action of UGT76G1 to generate rebaudioside A, a tetraglucoside of steviol, which is considered to be the sweetest (350 to 450 times sweeter than table sugar) and to have a good quality of taste.

Steviol glycosides are reported to improve their quality of taste and sweetness levels, particularly upon addition of a branched sugar to glucose at the 13-position (Non-patent Document 4, Patent Document 2). Thus, glycosyltransferases catalyzing these reactions would be important enzymes responsible for determining the sweetness properties of *stevia*.

Previous studies (Non-patent Document 2) have reported several types of glycosyltransferases (UGTs) as a result of EST analysis on *stevia* leaves, but detailed enzyme activity has not been fully examined for all of these enzymes.

PRIOR ART DOCUMENTS

Patent Documents

Patent Document 1: EP 1 897 951 B1
Patent Document 2: JP 5-255372 A

Non-Patent Documents

Non-patent Document 1: Brandle and Telmer (2007) Phytochemistry 68, 1855-1863
Non-patent Document 2: Richman et al (2005) Plant J. 41, 56-67
Non-patent Document 3: Mizutani and Ohta (2010) Annu. Rev. Plant Biol. 61, 291-315
Non-patent Document 4: Kasai et al (1981) Journal of the Chemical Society of Japan 5, 726-735

SUMMARY OF THE INVENTION

Problem to be Solved by the Invention

As a result of extensive and intensive efforts, the inventors of the present invention have succeeded in identifying an enzyme catalyzing sugar addition reaction to glucose at the 13-position of a steviol glycoside in *stevia*, as well as a gene sequence encoding this enzyme. The present invention is based on the above finding.

Means to Solve the Problem

Namely, the present invention is as follows.
[1] A protein of any one selected from the group consisting of (a) to (c) shown below:
(a) a protein which consists of the amino acid sequence shown in SEQ ID NO: 2;
(b) a protein which consists of an amino acid sequence with deletion, substitution, insertion and/or addition of 1 to 7 amino acids in the amino acid sequence shown in SEQ ID NO: 2 and which has the activity to add a sugar molecule(s) to —$OR_1$ at the 13-position and —$COOR_2$ at the 19-position of a compound represented by the following formula (I); and
(c) a protein which has an amino acid sequence sharing a sequence identity of 99% or more with the amino acid sequence shown in SEQ ID NO: 2 and which has the activity to add a sugar molecule(s) to —OR₁ at the 13-position and —COOR₂ at the 19-position of a compound represented by the following formula (I)

[Formula 1]

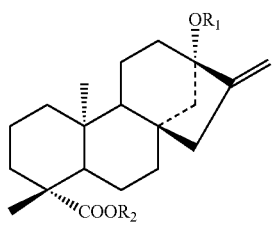

(I)

(wherein R₁ represents H, a glucose monomer or a glucose dimer, and R₂ represents H or a glucose monomer).

[2] The protein according to [1] above, wherein the sugar molecule is a hexose.

[3] The protein according to [1] above, wherein the sugar molecule is selected from the group consisting of glucose, mannose and galactose.

[4] The protein according to [1] above, wherein the compound is steviol, steviolmonoside, steviolbioside, rubusoside or Compound Y

[Formula 2]

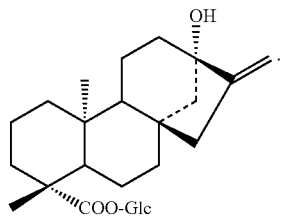

Compound Y

[5] A polynucleotide selected from the group consisting of (a) to (d) shown below:

(a) a polynucleotide containing the nucleotide sequence shown in SEQ ID NO: 1;

(b) a polynucleotide encoding a protein which consists of the amino acid sequence shown in SEQ ID NO: 2;

(c) a polynucleotide encoding a protein which consists of an amino acid sequence with deletion, substitution, insertion and/or addition of 1 to 7 amino acids in the amino acid sequence shown in SEQ ID NO: 2 and which has the activity to add a sugar molecule(s) to —OR₁ at the 13-position and —COOR₂ at the 19-position of a compound represented by the following formula (I); and (d) a polynucleotide encoding a protein which has an amino acid sequence sharing a sequence identity of 99% or more with the amino acid sequence shown in SEQ ID NO: 2 and which has the activity to add a sugar molecule(s) to —OR₁ at the 13-position and —COOR₂ at the 19-position of a compound represented by the following formula (I)

[Formula 3]

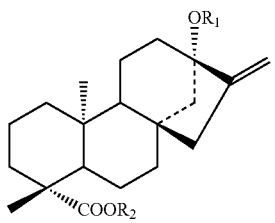

(I)

(wherein R₁ represents H, a glucose monomer or a glucose dimer, and R₂ represents H or a glucose monomer).

[6] The polynucleotide according to [5] above, wherein the sugar molecule is a hexose.

[7] The polynucleotide according to [5] above, wherein the sugar molecule is selected from the group consisting of glucose, mannose and galactose.

[8] The polynucleotide according to [5] above, wherein the compound is steviol, steviolmonoside, steviolbioside, rubusoside or Compound Y

[Formula 4]

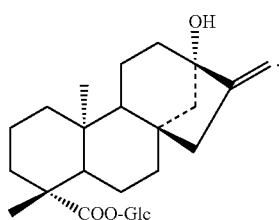

Compound Y

[9] A non-human transformant transformed with the polynucleotide according to [5] above.

[10] The transformant according to [9] above, wherein the polynucleotide is inserted into an expression vector.

[11] The transformant according to [9] above, which is a plant.

[12] An extract of the transformant according to [9] above.

[13] A food, a pharmaceutical preparation or an industrial raw material, which comprises the extract according to [12] above.

[14] A method for producing a protein, which comprises culturing the non-human transformant according to [9] above, wherein the protein has the activity to add a sugar molecule(s) to —OR₁ at the 13-position and —COOR₂ at the 19-position of a compound represented by the following formula (I)

[Formula 5]

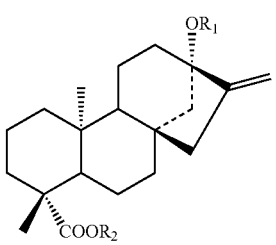

(I)

(wherein $R_1$ represents H, a glucose monomer or a glucose dimer, and $R_2$ represents H or a glucose monomer).

[15] A method for producing a steviol glycoside, which comprises using the non-human transformant according to [9] above.

[16] The method according to [15] above, wherein the steviol glycoside is steviolmonoside, steviolbioside, stevioside, rubusoside,

[Formula 6]

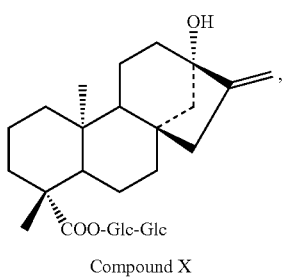

Compound X

[Formula 7]

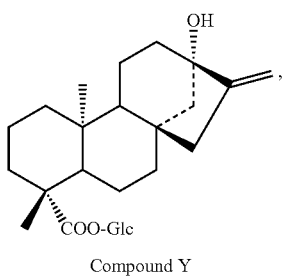

Compound Y

[Formula 8]

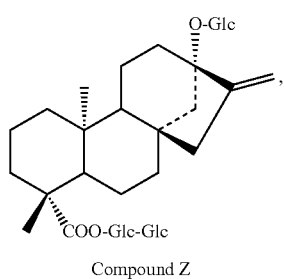

Compound Z or any combination thereof.

[17] A method for producing a steviol glycoside, which comprises the step of reacting the protein according to [1] above, a UDP-sugar and a compound represented by the following formula (I)

[Formula 9]

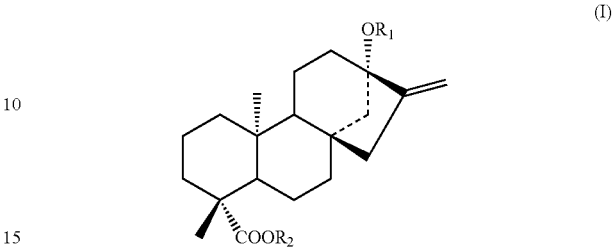

Compound X (wherein $R_1$ represents H, a glucose monomer or a glucose dimer, and $R_2$ represents H or a glucose monomer).

[18] The method according to [17] above, wherein the sugar in the UDP-sugar is glucose.

[19] The method according to [17] above, wherein the steviol glycoside is steviolmonoside, steviolbioside, stevioside, rubusoside,

[Formula 10]

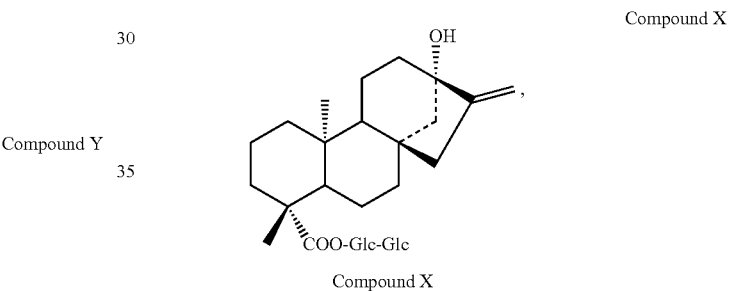

Compound X

[Formula 11]

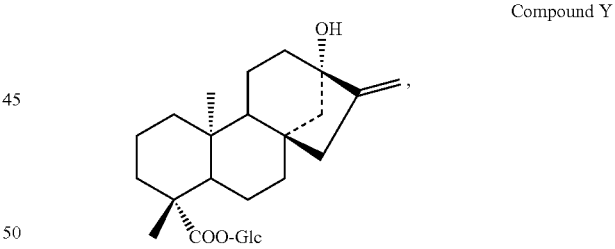

Compound Y

[Formula 12]

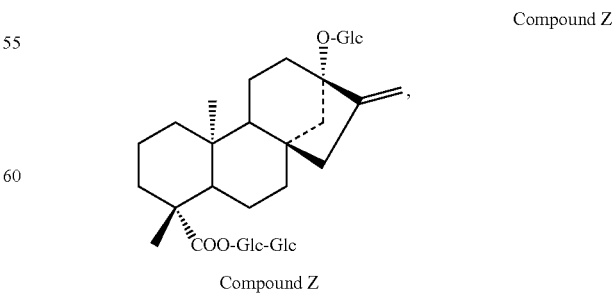

Compound Z or any combination thereof.

Effects of the Invention

The protein of the present invention and a polynucleotide encoding the same can be used for efficient production of steviol glycosides (e.g., steviolmonoside, steviolbioside, stevioside, rubusoside, Compound X, Compound Y, Compound Z). Moreover, the transformants of the present invention are rich in steviol glycosides (e.g., steviolmonoside, steviolbioside, stevioside, rubusoside, Compound X, Compound Y, Compound Z), and hence steviol glycosides (e.g., steviolmonoside, steviolbioside, stevioside, rubusoside, Compound X, Compound Y, Compound Z) can be efficiently extracted and purified from these transformants.

BRIEF DESCRIPTION OF THE DRAWINGS

FIG. 1 shows the names and structures of steviol glycoside members. In FIG. 1, "Glc" denotes glucose. Likewise, "Glc-Glc(β2→1)" denotes that "Glc-Glc" are linked to each other via a β2,1 glycosidic linkage, while "Glc-Glc(β3→1)" denotes that "Glc-Glc" are linked to each other via a β3,1 glycosidic linkage.

In FIG. 4, "Glc" denotes glucose.

In FIG. 6, "UGT73E1HP1" denotes UGT73E1 homologous protein 1.

Figure 2:
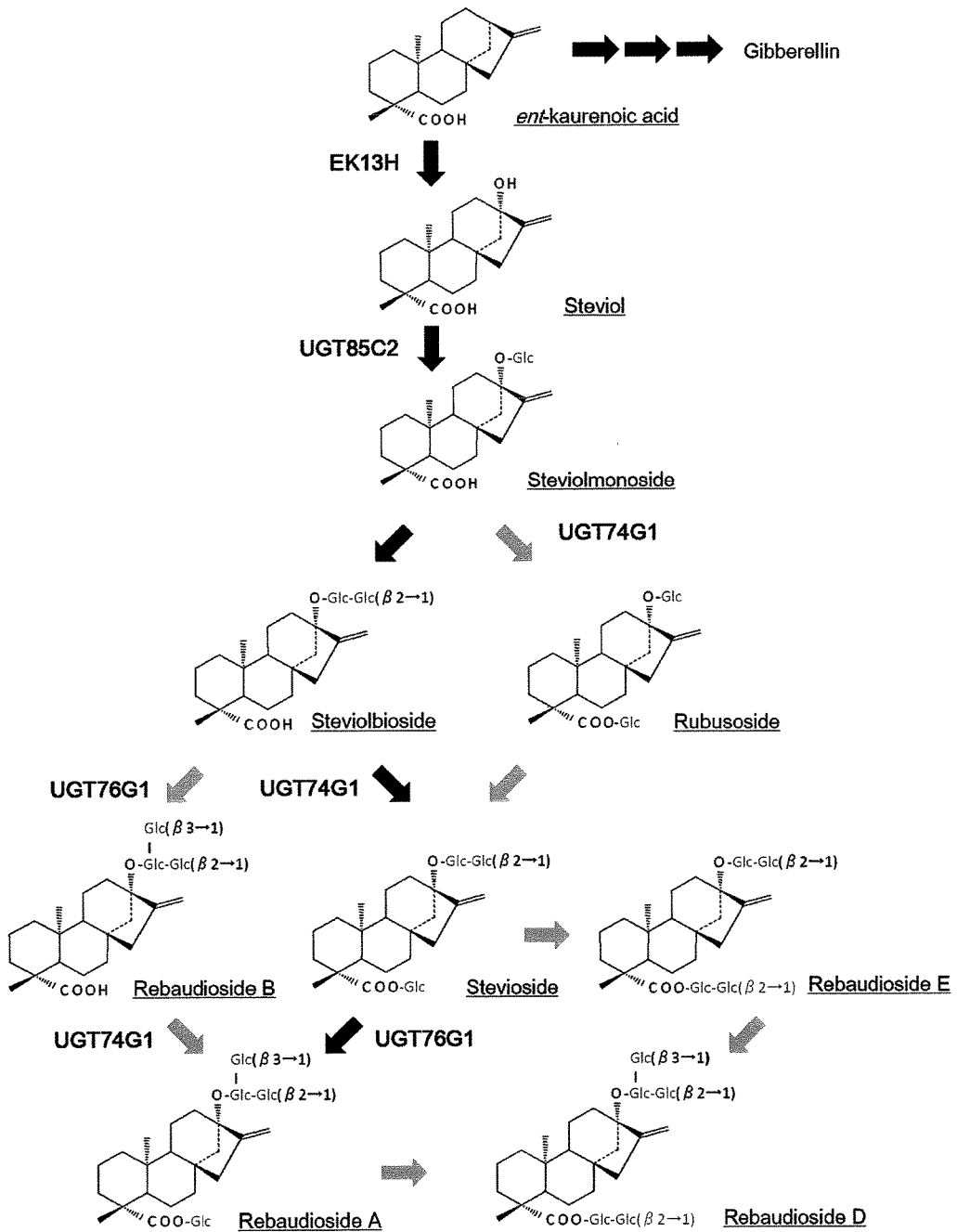
FIG. 2 shows putative biosynthetic pathways of steviol glycosides.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2012-123349 (filed on May 30, 2012), based on which the present application claims priority.

The present invention will be described in more detail below. The following embodiments are illustrated to describe the present invention, and it is not intended to limit the present invention only to these embodiments. The present invention can be implemented in various modes, without departing from the spirit of the present invention.

The inventors of the present invention have elucidated, ahead of others, that *stevia*-derived UGT73E1 homologous protein 1 is an enzyme protein responsible for sugar addition reaction in steviol glycosides toward the 13-position hydroxy group and glucose bound to the 13-position hydroxy group, as well as toward the 19-position carboxyl group and glucose bound to the 19-position carboxyl group.

The CDS sequence and deduced amino acid sequence of UGT73E1 homologous protein 1 are as shown in SEQ ID NOs: 1 and 2, respectively. The above polynucleotide and enzyme can be obtained by procedures as described later in the Example section, known genetic engineering procedures, known synthesis procedures, etc.

1. Steviol Glycosyltransferase

The present invention provides a protein of any one selected from the group consisting of (a) to (c) shown below (hereinafter referred to as "the protein of the present invention"):

(a) a protein which consists of the amino acid sequence shown in SEQ ID NO: 2;

(b) a protein which consists of an amino acid sequence with deletion, substitution, insertion and/or addition of 1 to 7 amino acids in the amino acid sequence shown in SEQ ID NO: 2 and which has the activity to add a sugar molecule(s) to —$OR_A$ at the 13-position and —$COOR2$ at the 19-position of a compound represented by the following formula (I); and (c) a protein which has an amino acid sequence sharing a sequence identity of 99% or more with the amino acid sequence shown in SEQ ID NO: 2 and which has the activity to add a sugar molecule(s) to —$OR_1$ at the 13-position and —$COOR_2$ at the 19-position of a compound represented by the following formula (I)

[Formula 13]

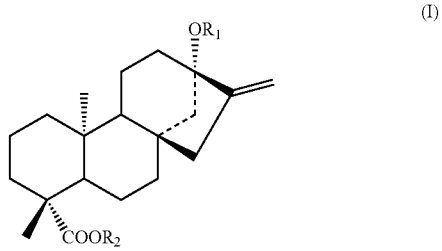

(I)

(wherein $R_1$ represents H, a glucose monomer or a glucose dimer, and $R_2$ represents H or a glucose monomer).

The above protein (b) or (c) is typically a mutant of the naturally occurring polypeptide shown in SEQ ID NO: 2, although other examples include those which may be artificially obtained by site-directed mutagenesis as described in "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the expression "protein which consists of an amino acid sequence with deletion, substitution, insertion and/or addition of 1 to 7 amino acids in the amino acid sequence shown in SEQ ID NO: 2 and which has the activity to add a sugar molecule(s) to —$OR_1$ at the 13-position and —$COOR_2$ at the 19-position of a compound represented by formula (I)" is intended to include proteins which consist of an amino acid sequence with deletion, substitution, insertion and/or addition of, e.g., 1 to 7 amino acid residues, 1 to 6 amino acid residues, 1 to 5 amino acid residues, 1 to 4 amino acid residues, 1 to 3 amino acid residues, 1 to 2 amino acid residues, or a single amino acid residue in the amino acid sequence shown in SEQ ID NO: 2 and which have the activity to add a sugar molecule(s) to —$OR_1$ at the 13-position and —$COOR_2$ at the 19-position of a compound represented by formula (I). In general, a smaller number is more preferred for the above deletion, substitution, insertion and/or addition of amino acid residues.

Moreover, examples of such proteins include those which have an amino acid sequence sharing a sequence identity of 99% or more, 99.1% or more, 99.2% or more, 99.3% or more, 99.4% or more, 99.5% or more, 99.6% or more, 99.7% or more, 99.8% or more, or 99.9% or more with the amino acid sequence shown in SEQ ID NO: 2 and which have the activity to add a sugar molecule(s) to —$OR_1$ at the 13-position and —$COOR_2$ at the 19-position of a compound represented by formula (I). In general, a larger value is more preferred for the above sequence identity.

In the context of the present invention, the expression "activity to add a sugar molecule(s) to —$OR_1$ at the 13-position and —$COOR_2$ at the 19-position of a compound represented by formula (I)" is intended to mean the ability to cause sugar addition to —$OR_1$ at the 13-position and —$COOR_2$ at the 19-position of a compound represented by the following formula (I).

[Formula 14]

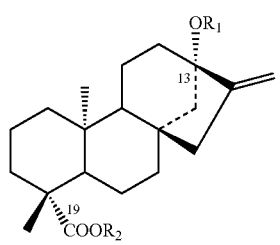

(I)

In formula (I), $R_1$ represents H, a glucose monomer (-Glc) or a glucose dimer (-Glc-Glc), and $R_2$ represents H or a glucose monomer (-Glc). Preferably, $R_2$ is H when $R_1$ is a glucose dimer. In the glucose dimer, glucoses are preferably linked to each other via a β2,1 glycosidic linkage. Moreover, sugar molecules to be added by the action of the protein of the present invention to —$OR_1$ at the 13-position and —$COOR_2$ at the 19-position of a compound represented by formula (I) are each preferably added via a β2,1 glycosidic linkage in both cases where $R_1$ is a glucose monomer or a glucose dimer and where $R_2$ is a glucose monomer.

A preferred compound of formula (I) is steviol, steviolmonoside, steviolbioside, rubusoside or Compound Y.

There is no particular limitation on the sugar molecules to be added by the action of the protein of the present invention to —$OR_1$ at the 13-position and —$COOR_2$ at the 19-position of a compound represented by formula (I), although they may be sugar molecules composed of one or more pentoses, hexoses or any combination thereof. Examples of pentoses and hexoses are as described above. The above sugar molecule is preferably a hexose, and more preferably a hexose selected from the group consisting of glucose, mannose and galactose. The above sugar molecule is most preferably glucose.

The activity to add a sugar molecule(s) to —$OR_1$ at the 13-position and —$COOR_2$ at the 19-position of a compound represented by formula (I) can be verified as follows: after incubation at a temperature of 20° C. to 40° C. for 10 minutes to 2 hours in a neutral buffer of pH 6.0 to 8.0 (e.g., sodium phosphate buffer or potassium phosphate buffer) which contains a test protein in an amount of 1 to 500 ng (preferably 50 to 200 ng, most preferably 100 ng), a UDP-sugar (e.g., UDP-glucose) at 1 to 1000 μM (preferably 100 to 700 μM, most preferably 500 μM) and a substrate compound (i.e., a compound of formula (I)) at 1 to 500 μM (preferably 100 to 500 μM, most preferably 250 μM), the above substrate compound is purified and analyzed by known procedures such as LC-MS analysis (liquid chromatography-mass spectrometry), etc.

If a compound having a sugar molecule(s) added to —$OR_1$ at the 13-position and —$COOR_2$ at the 19-position of a compound represented by formula (I) is detected as a result of LC-MS analysis, the above test protein can be regarded as having the activity to add a sugar molecule(s) to —$OR_1$ at the 13-position and —$COOR_2$ at the 19-position of a compound represented by formula (I).

The above sugar addition reaction is normally completed within about 1 minute to about 12 hours.

Deletion, substitution, insertion and/or addition of one or several amino acid residues in the amino acid sequence of the protein of the present invention is intended to mean that deletion, substitution, insertion and/or addition of one or several amino acid residues occurs at any one or more positions in the same sequence, and two or more of deletion, substitution, insertion and addition may occur at the same time.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Although the protein of the present invention may be obtained by being expressed from a polynucleotide encoding it (see "the polynucleotide of the present invention" described later) in appropriate host cells, it may also be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

2. Method for Producing a Steviol Glycoside

The present invention enables the production of steviol glycosides with ease and in large quantities by means of the activity of the protein to add a sugar molecule(s) to —$OR_1$ at the 13-position and —$COOR_2$ at the 19-position of a compound represented by formula (I).

In another embodiment, the present invention therefore provides a first method for producing a steviol glycoside, which comprises the step of reacting the protein of the present invention, a UDP-sugar and a compound represented by the following formula (I) to thereby add a sugar molecule(s) to either or both of —$OR_1$ at the 13-position and —$COOR_2$ at the 19-position of the compound represented by formula (I).

[Formula 15]

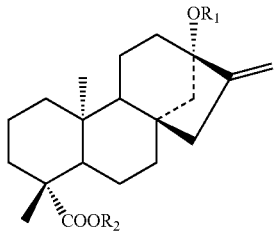

(I)

R₁ and R₂ in formula (I) are as defined above. A preferred compound of formula (I) is steviol, steviolmonoside, steviolbioside, rubusoside or Compound Y.

As used herein, the term "UDP-sugar" refers to a uridine diphosphate (UDP)-conjugated sugar. Preferred examples of the sugar moiety of a UDP-sugar include sugars composed of one or more pentoses, hexoses or any combination thereof. Examples of pentoses and hexoses are as described above. The UDP-sugar is preferably a UDP-hexose, and more preferably a hexose selected from the group consisting of glucose, mannose and galactose. The above UDP-sugar is most preferably UDP-glucose.

The first method for producing a steviol glycoside according to the present invention comprises the step of reacting the protein of the present invention, a UDP-sugar and a compound represented by formula (I) to thereby add a sugar molecule(s) to either or both of —OR₁ at the 13-position and —COOR₂ at the 19-position of the compound represented by formula (I). The first method of the present invention may further comprise the step of purifying the steviol glycoside generated in the above step.

Examples of a steviol glycoside produced by the first method include, but are not limited to, steviolmonoside, steviolbioside, stevioside, rubusoside, Compound X, Compound Y, Compound Z or any combination thereof.

The structure of Compound X is as shown below.

[Formula 16]

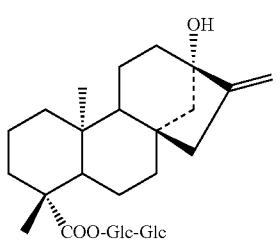

Compound X

The structure of Compound Y is as shown below.

[Formula 17]

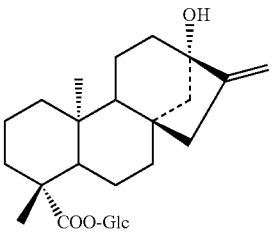

Compound Y

The structure of Compound Z is as shown below.

[Formula 18]

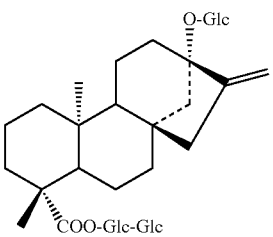

Compound Z

The generated steviol glycosides can be purified by known techniques such as extraction with an appropriate solvent (an aqueous solvent such as water or an organic solvent such as alcohol, ether or acetone), a gradient between an organic solvent (e.g., ethyl acetate) and water, high performance liquid chromatography (HPLC), gas chromatography, time-of-flight mass spectrometry (TOF-MS), ultra (high) performance liquid chromatography (UPLC), etc.

3. Non-Human Transformant Rich in Steviol Glycosides

Steviol glycosides may also be produced using the protein of the present invention within cells such as those of bacteria (e.g., *E. coli* or yeast), plants, insects, non-human mammals, etc. This is because the protein of the present invention is an enzyme derived from *stevia* or a mutant thereof and is therefore expected to have high activity even in the intracellular environment. In this case, a polynucleotide encoding the protein of the present invention (see "the polynucleotide of the present invention" described later) may be introduced into host cells derived from bacteria, plants, insects, non-human mammals or the like to cause expression of the protein of the present invention, followed by reacting the protein of the present invention with UDP-sugars and compounds represented by formula (I) present within the above cells to produce steviol glycosides.

[Formula 19]

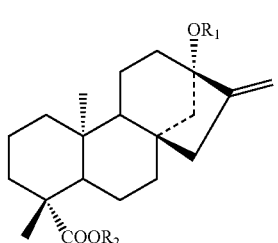

(I)

Then, the present invention provides a non-human transformant transformed with a polynucleotide of any one selected from the group consisting of (a) to (d) shown below (hereinafter referred to as "the polynucleotide of the present invention") (such a transformant is hereinafter referred to as "the transformant of the present invention"):

(a) a polynucleotide containing the nucleotide sequence shown in SEQ ID NO: 1;
(b) a polynucleotide encoding a protein which consists of the amino acid sequence shown in SEQ ID NO: 2;
(c) a polynucleotide encoding a protein which consists of an amino acid sequence with deletion, substitution, insertion and/or addition of 1 to 7 amino acids in the amino acid sequence shown in SEQ ID NO: 2 and which has the activity to add a sugar molecule(s) to —OR$_1$ at the 13-position and —COOR$_2$ at the 19-position of a compound represented by formula (I); and
(d) a polynucleotide encoding a protein which has an amino acid sequence sharing a sequence identity of 99% or more with the amino acid sequence shown in SEQ ID NO: 2 and which has the activity to add a sugar molecule(s) to —OR$_1$ at the 13-position and —COOR$_2$ at the 19-position of a compound represented by formula (I).

The definition and detailed examples of formula (I) are as already described above. Likewise, the definition and detailed examples of sugar molecules to be added to —OR$_1$ at the 13-position and —COOR$_2$ at the 19-position of a compound represented by formula (I) are as described above.

As used herein, the term "polynucleotide" is intended to mean DNA or RNA.

It should be noted that the sequence identity of amino acid sequences or nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, blastp, tblastn and tblastx have been developed (Altschul S F, et al: J Mol Biol 215: 403, 1990). If blastn is used for nucleotide sequence analysis, parameters may be set to, for example, score=100 and wordlength=12. Likewise, if blastp is used for amino acid sequence analysis, parameters may be set to, for example, score=50 and wordlength=3. If BLAST and Gapped BLAST programs are used, default parameters in each program may be used.

The above polynucleotides according to the present invention can be obtained by known genetic engineering procedures or known synthesis procedures.

The polynucleotide of the present invention is preferably introduced into a host in a state of being inserted into an appropriate expression vector.

An appropriate expression vector is generally configured to comprise:
(i) a promoter transcribable in host cells;
(ii) the polynucleotide of the present invention ligated to the promoter; and
(iii) an expression cassette comprising, as constituent elements, signals that function in the host cells for transcription termination and polyadenylation of an RNA molecule.

Such an expression vector may be prepared in any manner, for example, by techniques using plasmids, phages or cosmids, etc.

The actual type of vector is not limited in any way, and any vector expressible in host cells may be selected as appropriate. Namely, a promoter sequence may be selected as appropriate for the type of host cells in order to ensure expression of the polynucleotide of the present invention, and this promoter and the polynucleotide of the present invention may then be integrated into various plasmids or the like for use as expression vectors.

The expression vector of the present invention contains an expression control region(s) (e.g., a promoter, a terminator and/or a replication origin), depending on the type of host into which the expression vector is to be introduced. Promoters for use in bacterial expression vectors may be commonly used promoters (e.g., trc promoter, tac promoter, lac promoter). Likewise, promoters for use in yeast include, for example, glyceraldehyde triphosphate dehydrogenase promoter, PH05 promoter and so on, while promoters for use in filamentous fungi include, for example, amylase, trpC and so on. In addition, examples of promoters used to express a desired gene in plant cells include cauliflower mosaic virus 35S RNA promoter, rd29A gene promoter, rbcS promoter, and mac-1 promoter that is configured to have the enhancer sequence of the above cauliflower mosaic virus 35S RNA promoter at the 5'-side of *Agrobacterium*-derived mannopine synthase promoter sequence. Examples of promoters for use in animal cell hosts include viral promoters (e.g., SV40 early promoter, SV40 late promoter) and so on.

The expression vector preferably comprises at least one selection marker. For this purpose, auxotrophic markers (ura5, niaD), drug resistance markers (hygromycine, zeocin), geneticin resistance gene (G418r), copper resistance gene (CUP 1) (Mann et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991) and so on are available for use.

Although the transformant of the present invention may be prepared (produced) in any manner, an expression vector comprising the polynucleotide of the present invention may be introduced into a host to transform the host, by way of example.

The transformant of the present invention is expected to contain steviol glycosides at high contents. Host cells used for transformation may be of any type, and known various types of cells can be used preferably. Examples of host cells include bacteria such as *E. coli*, yeast (budding yeast *Saccharomyces cerevisiae*, fission yeast *Schizosaccharomyces pombe*), plant cells, non-human animal cells and so on.

Preferred host cells are those capable of producing a compound represented by formula (I). In the context of the present invention, host cells are not limited to those inherently capable of producing a compound represented by formula (I), and may also be, for example, those which have been recombinantly modified with a known gene to be able to produce a compound represented by formula (I).

Known examples of a gene encoding an enzyme contributing to the synthesis of a compound represented by formula (I) include, but are not limited to, EK13H, UGT74G1 and UGT76G1 (Non-patent Document 2).

In cases where host cells are not able to produce a compound represented by formula (I), these host cells are transformed with the gene of the present invention and the culture system of the resulting transformant is supplemented with, as a substrate, a compound of formula (I) or a plant extract containing this compound, whereby steviol glycosides can be produced without the need to introduce a gene encoding an enzyme contributing to the synthesis of a compound represented by formula (I).

Culture media and conditions appropriate for the above host cells are well known in the art. Moreover, the organism to be transformed may be of any type, and examples include various types of microorganisms or plants or non-human animals as listed above for host cells.

For transformation of host cells, commonly used known techniques can be used. For example, transformation may be accomplished by, but is not limited to, electroporation (Mackenxie, D. A. et al., Appl. Environ. Microbiol., vol. 66, p. 4655-4661, 2000), particle delivery method (described in JP 2005-287403 A), spheroplast method (Proc. Natl. Acad. Sci. USA, vol. 75, p. 1929, 1978), lithium acetate method (J. Bacteriology, vol. 153, p. 163, 1983), and other methods as described in Methods in yeast genetics, 2000 Edition: A Cold Spring Harbor Laboratory Course Manual.

In addition, as for standard molecular biological procedures, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

Upon culturing the thus obtained transformant, steviol glycosides can be accumulated within the transformant. As described above, the culture system of the transformant may be supplemented with, as a substrate, a compound of formula (I) or a plant extract containing this compound to thereby facilitate the production of steviol glycosides. The accumulated steviol glycosides may be extracted and purified to thereby obtain desired steviol glycosides.

Thus, the present invention provides a second method for producing a steviol glycoside, which comprises using the transformant of the present invention. Appropriate culture medium and conditions are well known in the art. Moreover, how to extract and purify steviol glycosides is as already described above.

Although steviol glycosides are not limited in any way, preferred are those which may be selected from the group consisting of steviolmonoside, steviolbioside, stevioside, rubusoside, Compound X, Compound Y, Compound Z and combinations thereof.

In one embodiment of the present invention, the transformant may be a plant transformant. The plant transformant according to this embodiment may be obtained by introducing a recombinant vector comprising the polynucleotide of the present invention into a plant such that a polypeptide encoded by this polynucleotide can be expressed.

In cases where a recombinant expression vector is used, any recombinant expression vector may be used for transformation of a whole plant as long as it is a vector allowing the polynucleotide of the present invention to be expressed within the plant. Examples of such a vector include those having a promoter which drives constitutive expression of a desired polynucleotide within plant cells or those having a promoter whose activation is induced by external stimulation.

Examples of a promoter which drives constitutive expression of a desired polynucleotide within plant cells include cauliflower mosaic virus 35S RNA promoter, rd29A gene promoter, rbcS promoter, mac-1 promoter, etc.

Examples of a promoter whose activation is induced by external stimulation include mouse mammary tumor virus (MMTV) promoter, tetracycline-responsive promoter, metallothionein promoter and heat shock protein promoter, etc.

The plant to be transformed in the present invention is intended to mean any of a whole plant, a plant organ (e.g., leaf, petal, stem, root, seed), a plant tissue (e.g., epidermis, phloem, parenchyma, xylem, vascular bundle, palisade tissue, spongy parenchyma) or a plant cultured cell, or alternatively, various forms of plant cells (e.g., suspension cultured cells), a protoplast, a leaf section, a callus and so on.

The plant used for transformation may be of any type, belonging to either monocotyledons or dicotyledons.

For gene transfer into plants, transformation techniques known to those skilled in the art may be used (e.g., *Agrobacterium*-mediated method, gene gun method, PEG-mediated method, electroporation). For example, *Agrobacterium*-mediated method and direct gene transfer into plant cells are well known. In the case of using the *Agrobacterium*-mediated method, the constructed plant expression vector may be introduced into an appropriate *Agrobacterium* strain (e.g., *Agrobacterium tumefaciens*) and this strain may then be infected into a leaf section cultured under sterile conditions, e.g., in accordance with the leaf disk method (Hirofumi Miyauchi, Manuals for Plant Genetic Engineering (1990) pages 27-31, Kodansha Scientific Ltd., Tokyo) to thereby obtain a transgenic plant. Alternatively, it is possible to use the method of Nagel et al. (Micribiol. Lett., 67: 325 (1990)). In this method, for example, an expression vector is first introduced into *Agrobacterium*, and the transformed *Agrobacterium* is then introduced into plant cells or plant tissues as described in Plant Molecular Biology Manual (Gelvin, S. B. et al., Academic Press Publishers). As used herein, the term "plant tissue" also includes a callus obtainable by culturing plant cells. In cases where the *Agrobacterium*-mediated method is used for transformation, a binary vector (e.g., pBI121 or pPZP202) may be used.

Likewise, techniques known for direct gene transfer into plant cells or plant tissues are electroporation and particle gun method. In the case of using a particle gun, a whole plant, a plant organ or a plant tissue may be used directly, or sections may be prepared therefrom before use, or protoplasts may be prepared and used. The thus prepared samples may be treated using a gene transfer device (e.g., PDS-1000 (BIO-RAD)). Although treatment conditions will vary depending on the type of plant or sample, the treatment is generally conducted at a pressure of about 450 to 2000 psi and at a distance of about 4 to 12 cm.

The transformed cells or plant tissues are first selected by drug resistance such as hygromycin resistance, and then regenerated into whole plants in a standard manner. Regeneration from transformed cells into whole plants may be accomplished by techniques known to those skilled in the art as appropriate for the type of plant cells.

In cases where cultured plant cells are used as a host, transformation may be accomplished by introducing a recombinant vector into the cultured cells with a gene gun or by electroporation, etc. Calli, shoots, hairy roots and the like obtained as a result of transformation may be used directly for cell culture, tissue culture or organ culture, and may also be regenerated into whole plants using conventionally known procedures for plant tissue culture, e.g., by being administered with an appropriate concentration of a plant hormone (e.g., auxin, cytokinin, gibberellin, abscisic acid, ethylene, brassinolide).

Confirmation of whether or not the polynucleotide of the present invention has been introduced into a plant may be accomplished by PCR, Southern hybridization, Northern hybridization, etc. For example, DNA is prepared from a transgenic plant and DNA specific primers are designed for PCR. PCR may be performed under the same conditions as used for preparation of the above plasmid. Then, amplification products may be subjected to, e.g., agarose gel electrophoresis, polyacrylamide gel electrophoresis or capillary electrophoresis, followed by staining with ethidium bromide, SYBR Green solution, etc. If the amplification products are detected as a single band, it can be confirmed that the plant has been transformed. Alternatively, primers which have been labeled with a fluorescent dye or the like may be used in PCR to thereby detect amplification products. Further, it is also possible to use techniques in which amplification products are bound onto a solid phase (e.g., a microplate) and confirmed by fluorescence or enzymatic reaction, etc.

Once a transgenic whole plant whose genome carries the polynucleotide of the present invention has been obtained, progeny plants may be obtained by sexual or asexual reproduction of the whole plant. Moreover, from such a whole plant or progeny plants thereof or clones thereof, for example, seeds, fruits, cuttings, tubers, root tubers, rootstocks, calli, protoplasts or the like may be obtained and used to achieve mass production of the whole plant. Thus, the present invention also encompasses a whole plant into which the polynucleotide of the present invention has been introduced in an expressible form, or progeny plants of the whole plant which have the same properties as the whole plant, or tissues derived from the whole plant and progeny plants thereof.

In addition, transformation techniques for various plants have already been reported. Transgenic plants according to the present invention include plants of the family Solanaceae (e.g., eggplant, tomato, hot pepper, potato, tobacco, *stramonium*, Chinese lantern plant, *petunia*, calibrachoa, nierembergia), plants of the family Leguminosae (e.g., soybean, adzuki bean, peanut, kidney bean, broad bean, Bird's foot trefoil), plants of the family Rosaceae (e.g., strawberry, Japanese apricot, cherry tree, rose, blueberry, blackberry, bilberry, cassis, raspberry, Chinese blackberry), plants of the family Caryophyllaceae (e.g., carnation, *gypsophila*), plants of the family Asteraceae (e.g., *chrysanthemum, gerbera*, sunflower, daisy, *stevia*), plants of the family Orchidaceae (e.g., orchid), plants of the family Primulaceae (e.g., cyclamen), plants of the family Gentianaceae (e.g., showy prairie gentian, gentian), plants of the family Iridaceae (e.g., freesia, iris, *gladiolus*), plants of the family Scrophulariaceae (e.g., snapdragon, torenia), stone crop (kalanchoe), plants of the family Liliaceae (e.g., lily, tulip), plants of the family Convolvulaceae (e.g., morning glory, ivy-leaved morning glory, moonflower, sweet potato, cypress vine, evolvulus), plants of the family Hydrangeaceae (e.g., *hydrangea*, deutzia), plants of the family Cucurbitaceae (e.g., bottle gourd), plants of the family Geraniaceae (e.g., *pelargonium*, geranium), plants of the family Oleaceae (e.g., weeping forsythia), plants of the family Vitaceae (e.g., grape), plants of the family Theaceae (e.g., *camellia*, tea plant), plants of the family Gramineae (e.g., rice, barley, wheat, oat, rye, maize, foxtail millet, Japanese barnyard millet, kaoliang, sugar cane, bamboo, wild oat, finger millet, sorghum, Manchurian wild rice, job's tears, pasture grass), plants of the family Moraceae (e.g., mulberry, hop, paper mulberry, rubber tree, *cannabis*), plants of the family Rubiaceae (e.g., coffee tree, *gardenia*), plants of the family Fagaceae (e.g., oak, beech, Japanese emperor oak), plants of the family Pedaliaceae (e.g., sesame), plants of the family Rutaceae (e.g., bitter orange, Citrus junos, satsuma mandarin, Japanese pepper tree), plants of the family Brassicaceae (e.g., red cabbage, flowering cabbage, Japanese radish, white shepherd's purse, Chinese colza, cabbage, broccoli, cauliflower), and plants of the family Lamiacea (e.g., *salvia, perilla*, lavender, skullcap). As examples particularly preferred as plants to be transformed, those known to biosynthesize various glycosides starting from steviol as an aglycon are desired for use, and examples of such plants include *stevia* and Chinese blackberry (*Rubus suavissimus*), etc.

When an appropriate substrate is present endogenously or added externally, the whole plant transformed with the polynucleotide of the present invention (hereinafter referred to as "the plant of the present invention" or "the whole plant of the present invention") is able to produce steviol glycosides in higher quantities than its wild-type counterpart.

The plant of the present invention can be easily obtained as a perfect whole plant by being grown from a seed, a cuttage, a bulb or the like of the plant of the present invention.

Thus, the plant of the present invention encompasses a whole plant, a plant organ (e.g., leaf, petal, stem, root, seed, bulb), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on.

4. Extract of Transformant and Use Thereof

In another embodiment, the present invention also provides an extract of the above transformant. When an appropriate substrate is present endogenously or added externally, the transformant of the present invention is rich in steviol glycosides as compared to its wild-type counterpart; and hence an extract of the transformant is considered to contain steviol glycosides at high concentrations.

Such an extract of the transformant of the present invention can be obtained as follows: the transformant is homogenized with, e.g., glass beads, a homogenizer or a sonicator and the resulting homogenate is centrifuged to collect the supernatant. In addition, a further extraction step may also be provided in accordance with extraction procedures for steviol glycosides as mentioned above.

The extract of the transformant of the present invention can be provided for use in, e.g., production of foods, pharmaceutical preparations and/or industrial raw materials according to standard practice.

In another embodiment, the present invention also provides a food, a pharmaceutical preparation and/or an industrial raw material (e.g., raw materials for foods), each containing the extract of the transformant of the present invention. Such a food, a pharmaceutical preparation and/or an industrial raw material, each containing the extract of the transformant of the present invention, may be prepared in a standard manner. In this way, such a food, a pharmaceutical preparation and/or an industrial raw material, each containing the extract of the transformant of the present invention, contains steviol glycosides generated by using the transformant of the present invention.

The pharmaceutical preparation (composition) of the present invention may be in any dosage form, such as solution, paste, gel, solid, powder and other dosage forms. Moreover, the pharmaceutical composition of the present invention may be used in external preparations for skin (e.g., oil, lotion, cream, emulsion, gel, shampoo, hair conditioner, nail enamel, foundation, lipstick, face powder, facial pack, ointment, powder, dentifrice, aerosol, cleansing foam), as well as bath preparations, hair growth promoters, skin essences, sunscreening agents and so on.

The pharmaceutical composition of the present invention may further comprise additional pharmaceutically active ingredients (e.g., anti-inflammatory ingredient) or auxiliary ingredients (e.g., lubricating ingredient, carrier ingredient), when required.

Examples of the food of the present invention include nutritional supplementary foods, health foods, functional foods, children's foods, geriatric foods and so on. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods.

In the food of the present invention, a calorie-less steviol glycoside is used as a sweetener. For this reason, the food of the present invention is low in calories and has the advantage of contributing to health promotion or health maintenance.

These foods and food products may be in the form of agricultural foods including bakery products, noodles, pastas, cooked rice, sweets (e.g., cake, ice cream, ice lollies, doughnuts, pastries, candies, chewing gums, gummies, tablets, as well as Japanese sweets such as rice dumplings (dango) and sweet bean paste buns (manju)), bean curd and processed products thereof; fermented foods including Japanese rice wine (sake), medicinal liquor, sweet cooking sherry (mirin), vinegar, soy sauce and miso (bean paste); livestock food products including yogurt, ham, bacon and sausage; seafood products including fish cake (kamaboko), deep-fried fish cake (ageten) and puffy fish cake (hanpen); as well as fruit drinks, soft drinks, sports drinks, alcoholic beverages, tea or flavor enhancers.

5. Screening Method for a Plant Rich in Steviol Glycosides

The present invention provides a screening method for a plant rich in steviol glycosides. More specifically, the above method comprises steps (1) to (3) shown below:
(1) the step of extracting mRNA from a test plant;
(2) the step of allowing hybridization between the above mRNA or cDNA prepared from the above mRNA and a polynucleotide which is hybridizable under high stringent conditions with a polynucleotide consisting of a nucleotide sequence complementary to the polynucleotide of the present invention; and
(3) the step of detecting the above hybridization.

The above step (1) may be accomplished by extracting mRNA from a test plant. Although mRNA may be extracted from any site of the test plant, preferred are petals. Once mRNA has been extracted, cDNA may be prepared from the mRNA through reverse transcription.

The above step (2) may be accomplished as follows: a polynucleotide or oligonucleotide consisting of a nucleotide sequence complementary to the polynucleotide of the present invention is used as a probe or primer and allowed to hybridize with the mRNA extracted above under high stringent conditions. As used herein, the term "high stringent conditions" refers to, for example, but is not limited to, the following conditions: (1) 5×SSC, 5×Denhardt's solution, 0.5% SDS, 50% formamide, 50° C.; (2) 0.2×SSC, 0.1% SDS, 60° C.; (3) 0.2×SSC, 0.1% SDS, 62° C.; or (4) 0.2×SSC, 0.1% SDS, 65° C. Under these conditions, it can be expected that DNA having a higher sequence identity is efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

Such a polynucleotide or oligonucleotide has a length of preferably 5 to 500 bp, more preferably 10 to 200 bp, and even more preferably 10 to 100 bp. The polynucleotide or oligonucleotide may be readily synthesized with various automatic synthesizers (e.g., AKTA oligopilot plus 10/100 (GE Healthcare)), or alternatively, its synthesis may be entrusted to a third party (e.g., Promega or Takara), etc.

When the polynucleotide consisting of a nucleotide sequence complementary to the polynucleotide of the present invention is used as a probe in the step (2), the step (3) may be accomplished by commonly used techniques for detection of hybridization, such as Southern blotting, Northern blotting (Sambrook, Fritsch and Maniatis, "Molecular Cloning: A Laboratory Manual" 2nd Edition (1989), Cold Spring Harbor Laboratory Press), microarrays (Affymetrix; see U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), or fluorescent in situ hybridization (FISH) (Sieben V. J. et al., (2007-06). IET Nanobiotechnology 1 (3): 27-35). On the other hand, when the polynucleotide consisting of a nucleotide sequence complementary to the polynucleotide of the present invention is used as a primer in the step (2), the step (3) may be accomplished by PCR amplification and the subsequent analysis of the resulting amplification products by electrophoresis or sequencing (Sambrook, Fritsch and Maniatis, "Molecular Cloning: A Laboratory Manual" 2nd Edition (1989), Cold Spring Harbor Laboratory Press), etc., to detect hybridization.

A whole plant in which hybridization was more often detected can be regarded as expressing higher levels of a protein having the activity to add a sugar molecule(s) to —OR$_1$ at the 13-position and —COOR$_2$ at the 19-position of a compound represented by the following formula (I) than other whole plants, and hence such a whole plant is predicted to be rich in steviol glycosides.

[Formula 20]

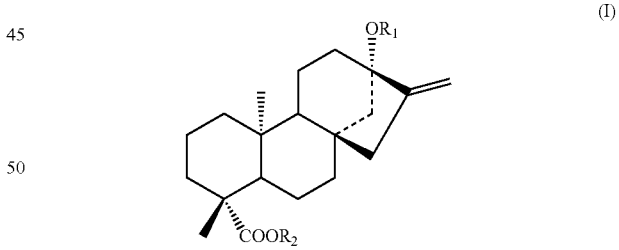

(I)

EXAMPLES

The present invention will now be described in more detail by way of the following examples, which are not intended to limit the scope of the present invention.

[Example 1] Isolation of Candidate Gene for Steviolbioside Glycosyltransferase

To obtain a gene highly homologous to UGT73E1 (AY345979) which has been reported to have no glycosylation activity on steviol glycosides in previous studies (Non-patent Document 2), cDNA prepared from *stevia* leaves was used as a template in PCR with the following primer set (SEQ ID NOs: 3 and 4).

The *stevia* leaf cDNA was obtained as follows: total RNA was extracted from *stevia* leaves with an RNeasy Plant Mini kit (QIAGEN), and 0.5 μg of the total RNA was then subjected to reverse transcription (RT) reaction with random oligo-dT primers.

```
CACC-NdeI-SrUGT73E1-Fw:
                                     (SEQ ID NO: 3)
5'-CACCCATATGTCGCCAAAAATGGTGGCACCA-3'

BamHI-SrUGT73E1-Rv:
                                     (SEQ ID NO: 4)
5'-GGATCCCTAATGTGGTGCTCTAACTGTTTCAGTCACAT-3'
```

A PCR reaction solution (50 μl) was prepared to consist of *stevia* leaf-derived cDNA (1 μl), 1×ExTaq buffer (Ta-KaRaBio), 0.2 mM dNTPs, primers (0.4 pmol/μl each) and ExTaq polymerase (2.5 U). The PCR reaction was accomplished by incubation at 94° C. for 3 minutes and the subsequent amplification in which reactions at 94° C. for 1 minute, at 50° C. for 1 minute and at 72° C. for 2 minutes were repeated for 30 cycles in total. The PCR products were electrophoresed on a 0.8% agarose gel and stained with ethidium bromide, thereby resulting in an amplified band at a size of approximately 1.5 kb predicted from each template DNA.

This PCR product was subcloned into pENTR-TOPO Directional vector (Invitrogen) in accordance with the method recommend by the manufacturer. The clone was sequenced by primer walking with synthetic oligonucleotide primers using a DNA Sequencer model 3100 (Applied Biosystems).

As a result of the sequence analysis of the cloned cDNA (designated as "UGT73E1 homologous protein 1"), it showed a sequence identity of 98% at the DNA level (a difference of 16 bases) and a sequence identity of 98% at the amino acid level (a difference of 8 amino acids) (CDS sequence: SEQ ID NO: 1, amino acid sequence: SEQ ID NO: 2) relative to the reported UGT73E1.

[Example 2] Construction of Expression Vector

An approximately 1.5 kb ORF fragment of UGT73E1 homologous protein 1 was excised by means of the NdeI and BamHI restriction enzyme sites (the underlined parts in SEQ ID NOs: 3 and 4) added to the primers and then was ligated to the NdeI and BamHI sites of an *E. coli* expression vector, pET15b (Novagen), to thereby obtain an *E. coli* expression vector for this enzyme gene. This vector was designed to carry the open reading frame of the UGT73E1 homologous protein 1 gene in frame with a His tag located upstream of the NdeI site of this vector and to express a chimeric protein fused between UGT73E1 homologous protein 1 and the His tag.

[Example 3] Expression and Purification of Recombinant Protein

To clarify biochemical functions of this enzyme, this enzyme was allowed to be expressed in *E. coli* cells. The UGT73E1 homologous protein 1 *E. coli* expression plasmid obtained above was used to transform *E. coli* strain BL21 (DE3) in a standard manner. The resulting transformant was cultured overnight at 37° C. under shaking conditions in 4 ml of a 50 μg/ml ampicillin-containing LB medium (10 g/l typtone pepton, 5 g/l yeast extract, 1 g/l NaCl). After reaching the resting phase, the cultured solution (4 ml) was inoculated into a medium of the same composition (80 ml) and cultured at 37° C. under shaking conditions. At the time point where the cell turbidity (OD600) reached about 0.5, IPTG was added at a final concentration of 0.5 mM, followed by culturing at 18° C. for 20 hours under shaking conditions.

The following manipulations were all performed at 4° C. The cultured transformant was collected by centrifugation (5,000×g, 10 min) and then added to and suspended in Buffer S [20 mM HEPES buffer (pH 7.5), 20 mM imidazole, 14 mM β-mercaptoethanol] at 1 ml/g cell. Subsequently, the suspension was homogenized by ultrasonication (15 sec, repeated 8 times) and then centrifuged (15,000×g, 15 min). The resulting supernatant was collected as a crude enzyme solution. The crude enzyme solution was loaded onto a His SpinTrap column (GE Healthcare) which had been equilibrated with Buffer S, followed by centrifugation (70×g, 30 sec). After washing with the buffer, proteins bound to the column were eluted stepwise with 5 ml each of Buffer S containing 100 mM and 500 mM imidazole. Each elution fraction was subjected to buffer replacement with 20 mM HEPES buffer (pH 7.5), 14 mM β-mercaptoethanol through a Microcon YM-30 unit (Amicon) (magnification of dialysis: ×1000).

Figure 3:
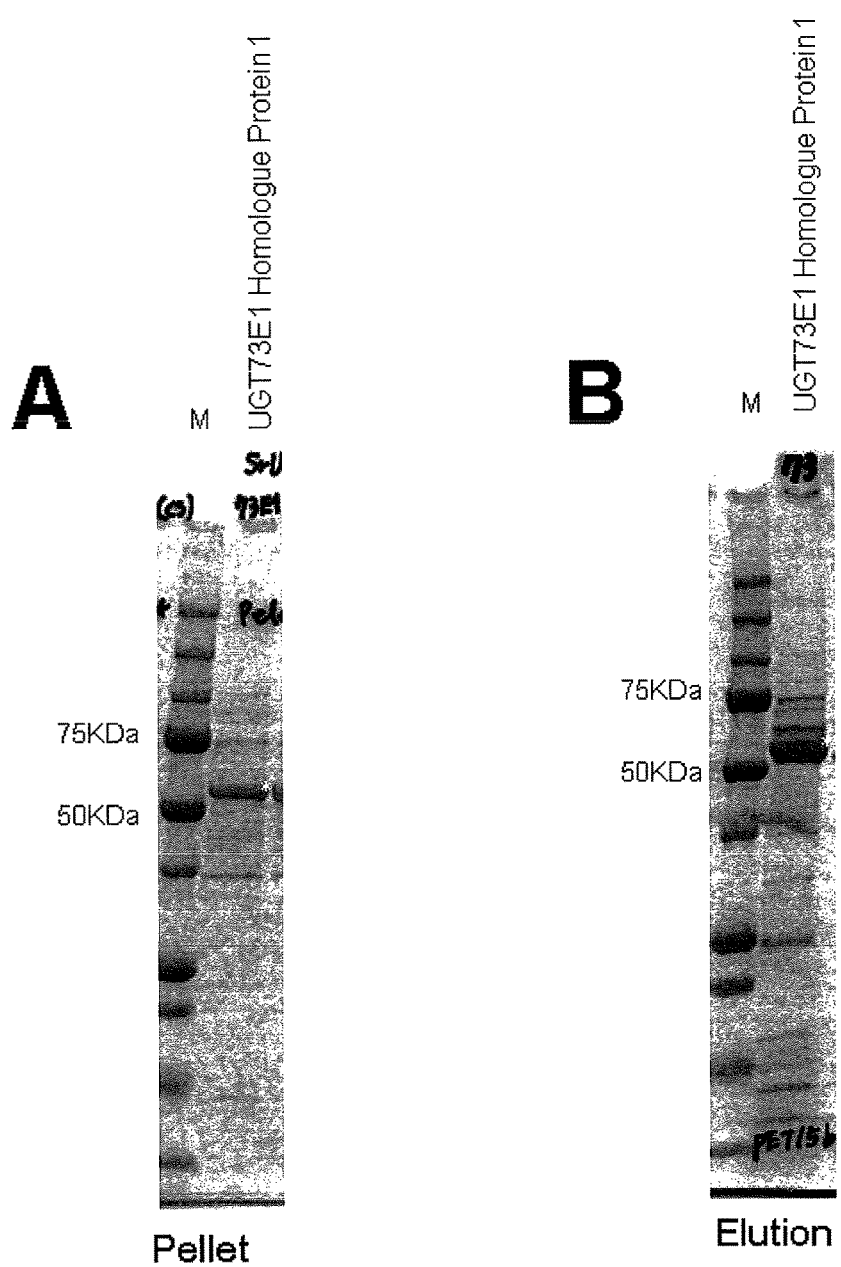
FIG. 3 shows the SDS-PAGE results obtained for UGT73E1 homologous protein 1 expressed in *E. coli*. Panel A shows a CBB-stained image obtained for the pellet fraction, while panel B shows a CBB-stained image obtained for the fraction eluted with an imidazole solution. The asterisks each represent an expressed recombinant protein.

As a result of SDS-PAGE separation and the subsequent CBB staining, in the fraction eluted with 200 mM imidazole, a protein was confirmed at approximately 50 kDa (indicated with an asterisk in FIG. 3), which is the putative molecular weight for the HisTag-fused UGT73E1 homologous protein 1 chimeric protein. This fraction was used for enzyme analysis. It should be noted that in FIG. 3, panel A shows a CBB-stained image obtained for the pellet fraction, while panel B shows a CBB-stained image obtained for the fraction eluted with the imidazole solution.

[Example 4] Measurement of Enzyme Activity of UGT73E1 Homologous Protein 1

Standard enzyme reaction conditions are as follows. A reaction solution (2 mM UDP-glucose, 0.1 mM sugar acceptor substrate (steviol), 100 mM potassium phosphate buffer (pH 7.0), 25 μl purified UGT73E1 homologous protein 1 enzyme solution) was prepared in a volume of 50 μl with distilled water and reacted at 30° C. for 1 hour. The enzyme reaction solution (5 μl) was analyzed by LC-MS under the following conditions.
LC conditions
Column: Waters Sunfire C18 3.5 um (2.0 mm I.D.×20 mm)
Mobile phase: A: MilliQ Water (+0.05% formic acid), B: MeCN
Gradient: linear concentration gradient of B from 15% to 55% over 20 minutes
Flow rate: 0.2 ml per minute
Column oven: 40° C.
MS conditions
ESI (negative mode)
Selected ion monitoring: m/z 317, 479, 641, 687, 803 and 849

Figure 4:
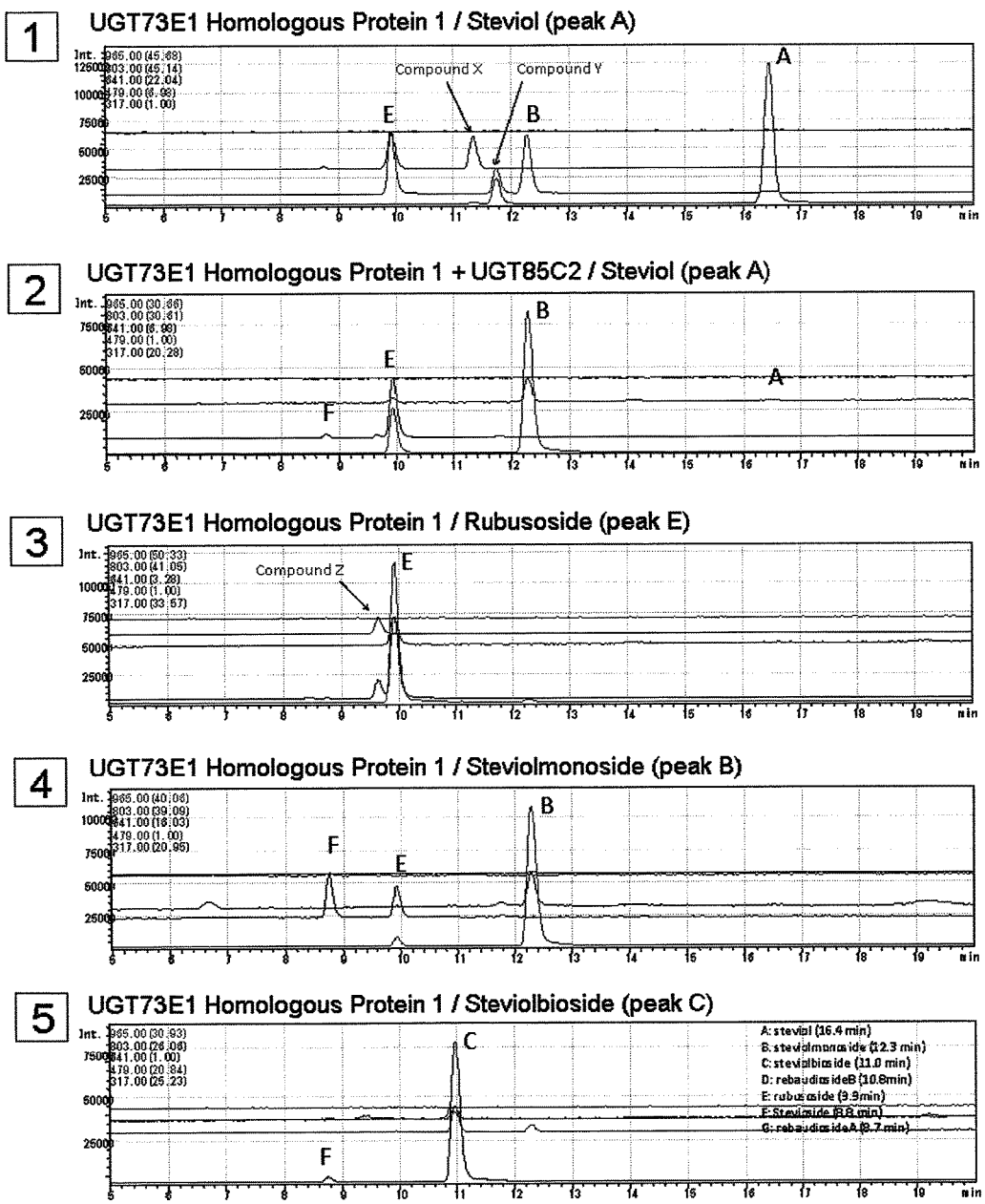
FIG. 4 shows the enzyme activity of UGT73E1 homologous protein 1.
Figure 5:
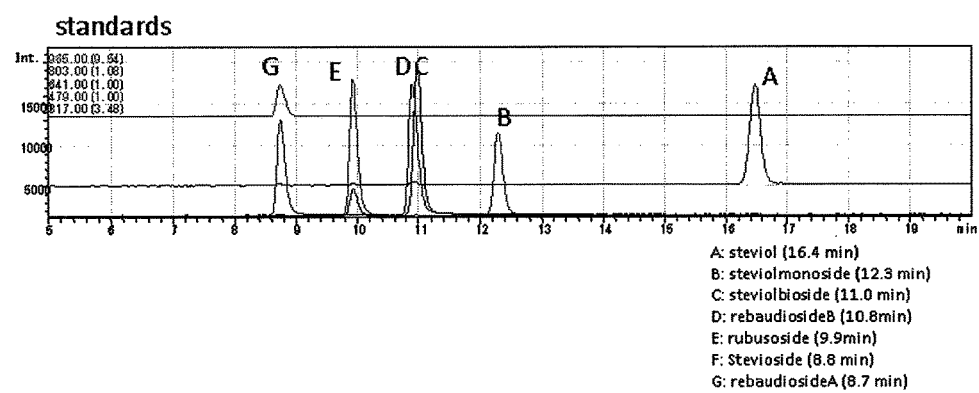
FIG. 5 shows a chromatogram obtained for reference standards of steviol and glycosides thereof.

As a result of the reaction between UGT73E1 homologous protein 1 and steviol, four types of products were newly found in the reaction solution between UGT73E1 homologous protein 1 and steviol (peak A) (FIG. 4: panel 1). Among them, peak E and peak B were identified to be rubusoside and steviolmonoside, respectively, based on comparison with the retention times of their reference standards (FIG. 5).

Figure 6:
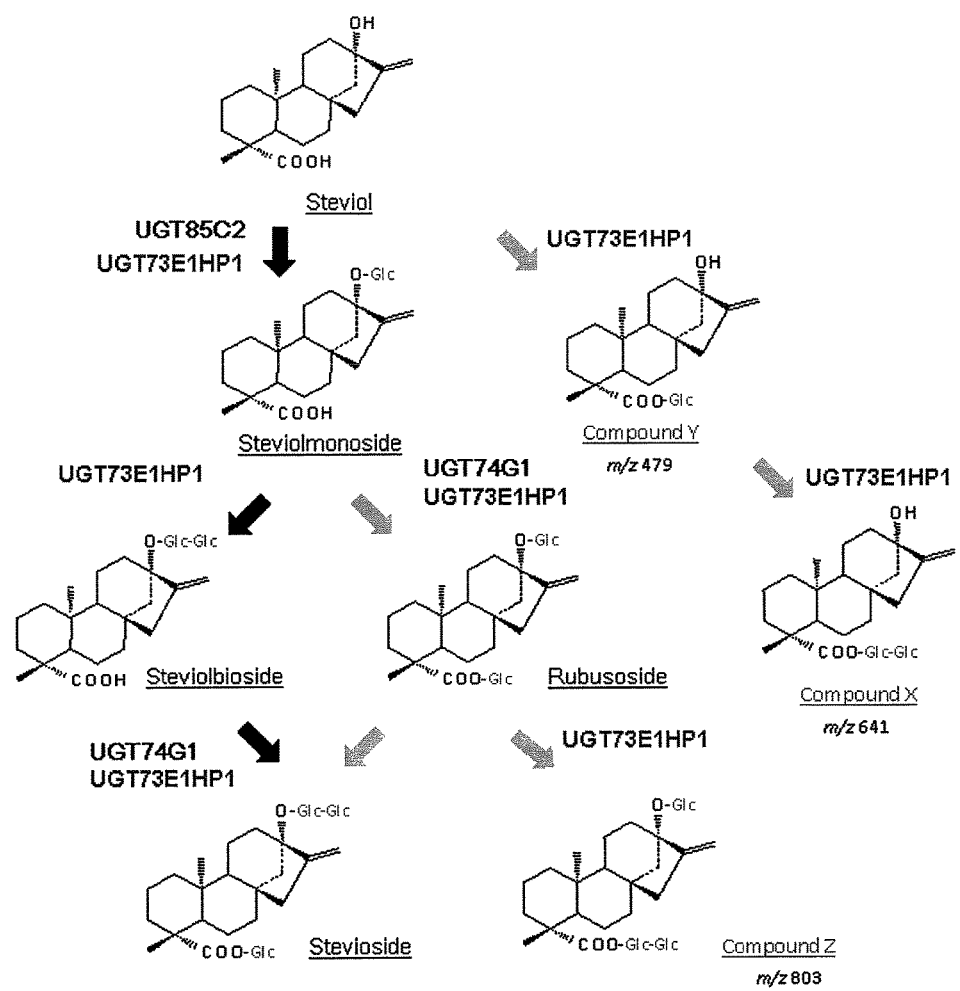
FIG. 6 shows reaction pathways catalyzed by UGT73E1 homologous protein 1.

On the other hand, with respect to the remaining two peaks, based on their MS chromatograms, Compound Y was identified to be a monoglucoside and Compound X was identified to be a diglucoside. The retention time of Compound Y was not in agreement with that of the reference standard steviolmonoside, thus suggesting that Compound Y was a monoglucoside in which the carboxyl group at the 19-position of steviol was monoglycosylated (FIG. 6). Likewise, the retention time of Compound X was not in agreement with that of steviolbioside or rubusoside, each being a diglucoside of steviol, thus strongly suggesting that the carboxyl group at the 19-position was glucosylated (FIG. 6). When UGT73E1 homologous protein 1 and UGT85C2 were simultaneously reacted with steviol (peak A), the peaks of Compound Y and Compound X were both reduced significantly (FIG. 4: panel 2). This would be because these two enzymes are in a competitive relationship where steviol is used in common as a substrate, and hence steviol (peak A) was rapidly converted into steviolmonoside (peak B) by the action of UGT85C2.

Furthermore, upon reaction between UGT73E1 homologous protein 1 and rubusoside (peak E), Compound Z which appears to be a triglucoside of steviol was newly generated (FIG. 4: panel 3). The retention time of Compound Z was not in agreement with those of stevioside and rebaudioside B (peaks F and D), each being a triglucoside of steviol, thus suggesting that the glucose at the 19-position of rubusoside was further glucosylated (FIG. 6).

Upon reaction between UGT73E1 homologous protein 1 and steviolmonoside (peak B), two peaks (peak E and peak F) were newly obtained (FIG. 4: panel 4). Based on their retention times, peak E was identified to be rubusoside and peak F was identified to be stevioside. Further, upon reaction between UGT73E1 homologous protein 1 and steviolbioside (peak C), a product which appears to be stevioside (peak F) was also detected (FIG. 4: panel 5).

In light of these results, UGT73E1 homologous protein 1 causes glucosylation at the 13-position hydroxy group of steviol to generate steviolmonoside, and causes further glucosylation at the 13-position glucose of steviolmonoside to generate steviolbioside, and causes further glucosylation at the 19-position carboxyl group of steviolbioside to generate stevioside. As shown above, UGT73E1 homologous protein 1 was found to have glucosylation activity on the 19-position of steviolmonoside to generate rubusoside. However, no significant stevioside peak can be found in the reaction solution between rubusoside and UGT73E1 homologous protein 1, thus suggesting that stevioside, a reaction product of UGT73E1 homologous protein 1, is generated via steviolbioside (FIG. 6).

INDUSTRIAL APPLICABILITY

In view of the foregoing, UGT73E1 homologous protein 1 was found to be a multifunctional glucosylation enzyme capable of reacting with steviol and various glucosides thereof (FIG. 6). This enzyme was found to be specific for different positions because it glucosylated steviol at the 13-position hydroxy group, further at the 19-position carboxyl group and further at the 19-position glucose. With the use of this enzyme, known steviol glycosides can be produced by a novel method. Moreover, structurally novel steviol glycosides can also be produced.

SEQUENCE LISTING FREE TEXT

SEQ ID NO: 3: synthetic DNA
SEQ ID NO: 4: synthetic DNA
Sequence Listing

The invention claimed is:
1. A polynucleotide selected from:
   a polynucleotide comprising the nucleotide sequence of SEQ ID NO: 1; and
   a polynucleotide comprising a heterologous regulatory element operably linked to a polynucleotide sequence encoding a protein consisting of the amino acid sequence of SEQ ID NO: 2.
2. A non-human transformant comprising the polynucleotide of claim 1.
3. The non-human transformant according to claim 2, which is a plant.
4. A method comprising culturing or cultivating the non-human transformant according to claim 2 to produce the protein consisting of the amino acid sequence of SEQ ID NO: 2.
5. The method of claim 4, further comprising:
   producing a steviol glycoside by contacting the protein consisting of the amino acid sequence of SEQ ID NO: 2 produced by the non-human transformant with a UDP-sugar and a compound represented by formula (I):

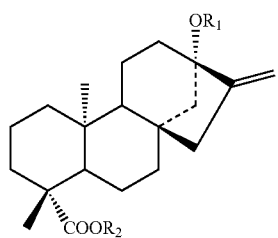

(I)

where:
   $R_1$ represents H, a glucose monomer, or a glucose dimer, and
   $R_2$ represents H or a glucose monomer.
6. A method for producing a steviol glycoside, comprising:
   contacting, outside of a *stevia* plant, a protein consisting of the amino acid sequence of SEQ ID NO: 2 with a UDP-sugar and a compound represented by formula (I):

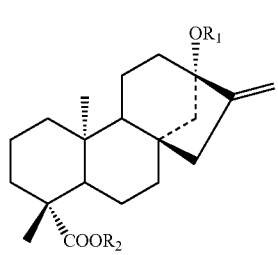

(I)

where:
   $R_1$ represents H, a glucose monomer, or a glucose dimer, and
   $R_2$ represents H or a glucose monomer.
7. The method according to claim 6, wherein the sugar in the UDP-sugar is a hexose.
8. The method according to claim 6, wherein the sugar in the UDP-sugar is selected from the group consisting of glucose, mannose, and galactose.
9. The method according to claim 6, wherein the compound is steviol, steviolmonoside, steviolbioside, rubusoside, or Compound Y:

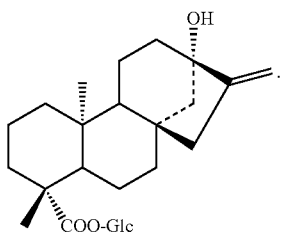

Compound Y

10. The method according to claim 6, wherein the sugar in the UDP-sugar is glucose.
11. The method according to claim 6, wherein the steviol glycoside is steviolmonoside, steviolbioside, stevioside, rubusoside, Compound X:

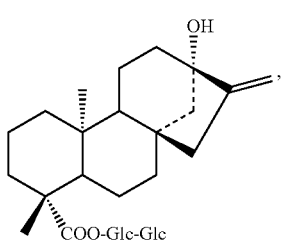

Compound X

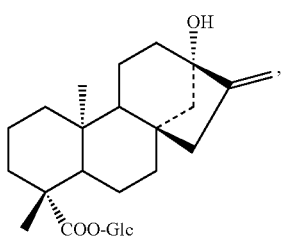

Compound Y

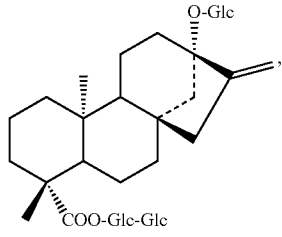

Compound Z or any combination thereof.
12. The non-human transformant according to claim 2, wherein the polynucleotide is inserted into an expression vector.
13. A method for producing an extract of the non-human transformant according to claim 2 or of a culture of the non-human transformant according to claim 2, the method comprising:
   providing the transformant according to claim 2 or the culture of the transformant, and obtaining an extract of the transformant or of the culture of the transformant.

14. A method for producing a food, a pharmaceutical preparation, or an industrial raw material, the method comprising:
providing an extract of the transformant according to claim 2 or of a culture of the transformant,
adding the extract to a raw material of a food, a pharmaceutical preparation, or an industrial raw material, and
preparing the food, the pharmaceutical preparation, or the industrial raw material.

15. The method according to claim 14, wherein the food is selected from fermented foods, fruit drinks, soft drinks, sports drinks, tea, bakery products, noodles, pastas, cooked rice, sweets, bean curd, ham, bacon, sausage, fish cake (kamaboko), deep-fried fish cake (ageten), and puffy fish cake (hanpen).

16. The method according to claim 15, wherein the fermented foods include alcoholic beverages, tea, medicinal liquor, sweet cooking sherry (mirin), vinegar, soy sauce, miso (bean paste), and yogurt.

17. The method according to claim 14, wherein the pharmaceutical preparation is selected from cream, gel, lipstick, facial pack, ointment, dentifrice, and cleansing foam.

\* \* \* \* \*

SEQUENCE LISTING

```
<160> NUMBER OF SEQ ID NOS: 4

<210> SEQ ID NO 1
<211> LENGTH: 1488
<212> TYPE: DNA
<213> ORGANISM: Stevia rebaudiana
<220> FEATURE:
<221> NAME/KEY: CDS
<222> LOCATION: (1)..(1485)

<400> SEQUENCE: 1 atg tcg cca aaa atg gtg gca cca cca acc aac ctt cat ttt gtt ttg      48
Met Ser Pro Lys Met Val Ala Pro Pro Thr Asn Leu His Phe Val Leu
1               5                   10                  15 ttt cct ctt atg gct caa ggc cat ctg gta ccc atg gtc gac atc gct      96
Phe Pro Leu Met Ala Gln Gly His Leu Val Pro Met Val Asp Ile Ala
                20                  25                  30 cga atc tta gcc caa cgt ggt gca acg gtc acc ata atc acc aca ccc     144
Arg Ile Leu Ala Gln Arg Gly Ala Thr Val Thr Ile Ile Thr Thr Pro
            35                  40                  45 tac gat gcc aac cgg gtc aga ccg gtt atc tcc cga gcc atc gcg acc     192
Tyr Asp Ala Asn Arg Val Arg Pro Val Ile Ser Arg Ala Ile Ala Thr
        50                  55                  60 aat ctc aag atc cag cta ctc gaa ctc caa ctg cgg tca acc gaa gcc     240
Asn Leu Lys Ile Gln Leu Leu Glu Leu Gln Leu Arg Ser Thr Glu Ala
65                  70                  75                  80
```

-continued

| | |
|---|---|
| ggt tta ccc gaa ggg tgc gaa agc ttc gac caa ctt ccg tca ttc gag<br>Gly Leu Pro Glu Gly Cys Glu Ser Phe Asp Gln Leu Pro Ser Phe Glu<br>                    85                              90                          95 | 288 |
| tac tgg aaa aat att tca acc gct atc cat ttg tta caa caa ccc gct<br>Tyr Trp Lys Asn Ile Ser Thr Ala Ile His Leu Leu Gln Gln Pro Ala<br>                100                            105                        110 | 336 |
| gaa gat ttg ctc cga gaa ctt tca cca cca ccc gat tgc atc ata tcg<br>Glu Asp Leu Leu Arg Glu Leu Ser Pro Pro Pro Asp Cys Ile Ile Ser<br>              115                           120                        125 | 384 |
| gac ttt tgg ttc ccg tgg acc acc gat gtg gct cga cgg tta aac atc<br>Asp Phe Trp Phe Pro Trp Thr Thr Asp Val Ala Arg Arg Leu Asn Ile<br>130                        135                            140 | 432 |
| ccc cgg ctc gtg ttc aac gga aag ggc tgc ttt tat ccc ttg tgc atg<br>Pro Arg Leu Val Phe Asn Gly Lys Gly Cys Phe Tyr Pro Leu Cys Met<br>145                        150                            155                        160 | 480 |
| cat gtt gcg atc act tcc aac att ttg gga gag aat gaa ccg gtc agt<br>His Val Ala Ile Thr Ser Asn Ile Leu Gly Glu Asn Glu Pro Val Ser<br>                165                            170                        175 | 528 |
| agt aat acc gag cgc gtt gtg ctg ccc ggt tta cct gac cgg atc gaa<br>Ser Asn Thr Glu Arg Val Val Leu Pro Gly Leu Pro Asp Arg Ile Glu<br>                  180                            185                        190 | 576 |
| gtc act aaa ctt cag atc ctc ggt tcg tcg aga cca gcc aac gta gac<br>Val Thr Lys Leu Gln Ile Leu Gly Ser Ser Arg Pro Ala Asn Val Asp<br>                    195                            200                      205 | 624 |
| gaa atg ggc tcg tgg ctt cga gcc gta gaa gcc gag aaa gct tca ttc<br>Glu Met Gly Ser Trp Leu Arg Ala Val Glu Ala Glu Lys Ala Ser Phe<br>210                        215                            220 | 672 |
| ggg ata gtg gtt aat act ttc gaa gag ctt gaa ccg gag tac gtt gaa<br>Gly Ile Val Val Asn Thr Phe Glu Glu Leu Glu Pro Glu Tyr Val Glu<br>225                        230                            235                        240 | 720 |
| gaa tac aaa acg gtt aaa gat aag aag atg tgg tgt atc ggc ccg gtt<br>Glu Tyr Lys Thr Val Lys Asp Lys Lys Met Trp Cys Ile Gly Pro Val<br>                245                            250                        255 | 768 |
| tcg tta tgc aac aaa acc ggg ccg gat tta gcc gag cga gga aac aag<br>Ser Leu Cys Asn Lys Thr Gly Pro Asp Leu Ala Glu Arg Gly Asn Lys<br>                  260                            265                        270 | 816 |
| gct gca ata acc gaa cac aac tgc tta aaa tgg ctc gat gag aga aaa<br>Ala Ala Ile Thr Glu His Asn Cys Leu Lys Trp Leu Asp Glu Arg Lys<br>                275                            280                        285 | 864 |
| ctg ggg tcc gtg tta tac gtt tgt tta ggt agc ctt gca cgc att tct<br>Leu Gly Ser Val Leu Tyr Val Cys Leu Gly Ser Leu Ala Arg Ile Ser<br>                290                            295                        300 | 912 |
| acc gca caa gca atc gag ctc ggg tta gga ctc gag tcc ata aac cga<br>Thr Ala Gln Ala Ile Glu Leu Gly Leu Gly Leu Glu Ser Ile Asn Arg<br>305                        310                            315                        320 | 960 |
| ccc ttt ata tgg tgc gta aga aac gaa acc gat gag ctc aaa aca tgg<br>Pro Phe Ile Trp Cys Val Arg Asn Glu Thr Asp Glu Leu Lys Thr Trp<br>                    325                            330                        335 | 1008 |
| ttt ttg gat ggg ttt gaa gaa agg gtt aga gat cgc ggg ttg atc gtt<br>Phe Leu Asp Gly Phe Glu Glu Arg Val Arg Asp Arg Gly Leu Ile Val<br>                340                            345                        350 | 1056 |
| cat ggt tgg gcg cca cag gtt ttg ata ctg tcg cac cca acc att ggc<br>His Gly Trp Ala Pro Gln Val Leu Ile Leu Ser His Pro Thr Ile Gly<br>                355                            360                        365 | 1104 |
| ggt ttc ttg acc cat tgc ggt tgg aac tcg act att gaa tcg att acc<br>Gly Phe Leu Thr His Cys Gly Trp Asn Ser Thr Ile Glu Ser Ile Thr<br>370                        375                            380 | 1152 |
| gcg ggt gtt cca atg atc acg tgg ccg ttt ttt gcg gac cag ttt ttg<br>Ala Gly Val Pro Met Ile Thr Trp Pro Phe Phe Ala Asp Gln Phe Leu<br>385                        390                            395                        400 | 1200 |

```
aat gaa gct ttt ata gtt gaa gtt ttg aag att gga gtt agg att ggt      1248
Asn Glu Ala Phe Ile Val Glu Val Leu Lys Ile Gly Val Arg Ile Gly
                405                 410                 415 gtt gag aga gct tgt tcg ttt ggg gaa gaa gat aag gtt gga gtg ttg      1296
Val Glu Arg Ala Cys Ser Phe Gly Glu Glu Asp Lys Val Gly Val Leu
            420                 425                 430 gtg aag aag gag gat gtg aaa aag gct gtt gaa tgc ttg atg gat gaa      1344
Val Lys Lys Glu Asp Val Lys Lys Ala Val Glu Cys Leu Met Asp Glu
        435                 440                 445 gat gaa gat ggt gat cag aga aga aag agg gtg att gag ctt gca aaa      1392
Asp Glu Asp Gly Asp Gln Arg Arg Lys Arg Val Ile Glu Leu Ala Lys
    450                 455                 460 atg gcg aag att gca atg gcg gaa ggt gga tct tct tat gaa aat gta      1440
Met Ala Lys Ile Ala Met Ala Glu Gly Gly Ser Ser Tyr Glu Asn Val
465                 470                 475                 480 tcg tcg ttg att cga gat gtg act gaa aca gtt aga gca cca cat tag     1488
Ser Ser Leu Ile Arg Asp Val Thr Glu Thr Val Arg Ala Pro His
                485                 490                 495

<210> SEQ ID NO 2
<211> LENGTH: 495
<212> TYPE: PRT
<213> ORGANISM: Stevia rebaudiana

<400> SEQUENCE: 2

Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr Asp Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile His Leu Leu Gln Gln Pro Ala
            100                 105                 110

Glu Asp Leu Leu Arg Glu Leu Ser Pro Pro Asp Cys Ile Ile Ser
        115                 120                 125

Asp Phe Trp Phe Pro Trp Thr Thr Asp Val Ala Arg Arg Leu Asn Ile
    130                 135                 140

Pro Arg Leu Val Phe Asn Gly Lys Gly Cys Phe Tyr Pro Leu Cys Met
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Arg Ile Glu
            180                 185                 190

Val Thr Lys Leu Gln Ile Leu Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
```

```
            245                 250                 255
Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
            275                 280                 285

Leu Gly Ser Val Leu Tyr Val Cys Leu Gly Ser Leu Ala Arg Ile Ser
            290                 295                 300

Thr Ala Gln Ala Ile Glu Leu Gly Leu Gly Leu Ser Ile Asn Arg
305                 310                 315                 320

Pro Phe Ile Trp Cys Val Arg Asn Glu Thr Asp Glu Leu Lys Thr Trp
            325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
            355                 360                 365

Gly Phe Leu Thr His Cys Gly Trp Asn Ser Thr Ile Glu Ser Ile Thr
            370                 375                 380

Ala Gly Val Pro Met Ile Thr Trp Pro Phe Phe Ala Asp Gln Phe Leu
385                 390                 395                 400

Asn Glu Ala Phe Ile Val Glu Val Leu Lys Ile Gly Val Arg Ile Gly
            405                 410                 415

Val Glu Arg Ala Cys Ser Phe Gly Glu Glu Asp Lys Val Gly Val Leu
            420                 425                 430

Val Lys Lys Glu Asp Val Lys Lys Ala Val Glu Cys Leu Met Asp Glu
            435                 440                 445

Asp Glu Asp Gly Asp Gln Arg Arg Lys Arg Val Ile Glu Leu Ala Lys
            450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
            485                 490                 495

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacccatatg tcgccaaaaa tggtggcacc a                                    31

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatccctaa tgtggtgctc taactgtttc agtcacat                             38
```